US006068848A

United States Patent [19]
Gubernick et al.

[11] Patent Number: 6,068,848
[45] Date of Patent: May 30, 2000

[54] ANTIOXIDANT MIXTURE COMPRISING TOCOPHEROL

[75] Inventors: Joseph Gubernick, New York; Kenneth D. Marenus, Dix Hills; Edward Pelle, Valley Stream, all of N.Y.; Lieve Declercq, Ekeren, Belgium; Daniel H. Maes, Huntington, N.Y.

[73] Assignee: Color Access, Inc., Melville, N.Y.

[21] Appl. No.: 08/992,128

[22] Filed: Dec. 17, 1997

[51] Int. Cl.[7] .............................. A61K 6/00; A61K 7/42
[52] U.S. Cl. ............................ 424/401; 424/59; 424/69; 424/63
[58] Field of Search .......................... 424/401, 63, 448, 424/59, 69

[56] References Cited

U.S. PATENT DOCUMENTS

| | | |
|---|---|---|
| 3,903,317 | 9/1975 | Cort . |
| 4,003,919 | 1/1977 | Scott et al. . |
| 4,018,799 | 4/1977 | Scott et al. . |
| 4,026,907 | 5/1977 | Scott et al. . |
| 5,230,916 | 7/1993 | Chang et al. ............................ 424/330 |
| 5,296,500 | 3/1994 | Hillebrand ............................ 514/562 |
| 5,376,361 | 12/1994 | Perricone ................................ 424/59 |
| 5,616,332 | 4/1997 | Herstein ................................ 424/401 |
| 5,621,012 | 4/1997 | Schonrock et al. ...................... 514/629 |
| 5,658,556 | 8/1997 | Gers-Barlag et al. .................... 424/63 |
| 5,723,482 | 3/1998 | Degwert et al. ........................ 514/399 |
| 5,811,083 | 9/1998 | Pelle et al. ............................... 424/59 |

FOREIGN PATENT DOCUMENTS

| | | |
|---|---|---|
| 0 659 402 | 6/1995 | European Pat. Off. . |
| 88/03015 | 5/1988 | WIPO . |
| WO 93/10755 | 6/1993 | WIPO . |

OTHER PUBLICATIONS

Packer, L.; C.A. Rice–Evans and R.H. Burdon: (Eds.), Free Radical Damage and its Control, 1994 Elsevier Science B.V., 9: pp. 239–255, Ultraviolet Radiation (UVA, UVB) and Skin Antioxidants.

Miyachi, et al., Clinical and Experimental Dermatology (1983) 8: pp. 305–310, Sunburn Cell Formation is Prevented by Scavenging Oxygen Intermediates.

Khettab, et al., Biochimie 70: pp. 1709–1713, 1988, Photoprotective Effect of Vitamins A and E on Polyamine and Oxygenated Free Radical Metabolism in Hairless Mouse Epidermis.

E. Law & A.J. Lewis, Br. J. Pharmacol. 59:pp. 591–597, 1977, The Effect of Systemically and Topically Applied Drugs on Ultraviolet–Induced Erythema in the Rat.

Bissett, et al., Photodermatol. Photoimmunol. Photomed. 7: pp. 56–62, 1990, Photoprotective Effect of Superoxide–S-cavenging Antioxidants Against Ultraviolet Radiation–Induced Chronic Skin Damage in the Hairless Mouse.

Patent Abstracts of Japan, vol. 010, No. 178 (C–355), Jun. 21, 1986 & JP 61 027910 A (KAO Corp), Feb. 7, 1986.

*Primary Examiner*—Thurman K. Page
*Assistant Examiner*—Susan Tran
*Attorney, Agent, or Firm*—Kenyon & Kenyon

[57] ABSTRACT

The present invention relates to cosmetic or pharmaceutical compositions for topical application to the skin, the compositions comprising effective amounts of at least one of each of the antioxidants selected from the group consisting of (a) tocopherol and derivatives thereof, (b) ascorbic acid and derivatives thereof,(c) a butylated phenol, (d)N-acetyl cysteine, (e)a rosemary extract, and (f)ubiquinone and derivatives thereof. The compositions are useful in treating and preventing the symptoms of photoaging.

15 Claims, 11 Drawing Sheets

ANTIOXIDANT MIXTURE COMPRISING TOCOPHEROL

FIELD OF THE INVENTION

The invention relates to cosmetic and pharmaceutical compositions for topical application to the skin. More specifically, the invention relates to compositions useful in preventing and treating the signs of extrinsic aging in the skin.

BACKGROUND OF THE INVENTION

It has now long been recognized that there is a cause-and-effect relationship between prolonged and/or repeated exposure to UV light and premature aging of the skin. In general terms, excessive exposure to the sun contributes substantially to premature decline in the quality and quantity of elastin and collagen in the skin, as well as hypertrophy of the epidermis. These changes are manifested externally by typical signs of aging, such as deep lines and wrinkles, loss of elasticity, skin dryness and unevenness, and increased frequency of blotches, pigmented spots, and benign as well as malignant neoplasms.

It has also been proposed that to a large extent the damage done is due to the generation of free radical species on the skin by UV radiation, Free radicals, if uncontrolled, may rapidly, and randomly, react with molecules in their vicinity, giving rise to toxic products that can interfere with the body's normal physiological processes. The cumulative effects of these reactions can, and probably always eventually do, overwhelm the body's normal repair mechanisms. Free radical reactions are widely considered to have a major contributory effect on the natural aging process.

It has been recognized in recent years that the presence of oxygen radicals on the skin is probably responsible for a number of the undesirable effects of exposure to the sun. For example, the aging phenomenon generally observed throughout the body is frequently observed prematurely on the skin as a result of photoaging, which accelerates the process of deterioration of elastin and collagen, among other effects. There is also an increased risk of skin cancer of all types. In response to this need, the skin care industry has continued to seek new and more effective means for combating the these processes. Antioxidants in general have not, to date, been shown to have an in vivo protective effect on human skin against a routine, non-acute exposure to sun, and there has been much skepticism as to whether antioxidants can really be expected to have measurable effect on the aging process. There thus continues to be a need for a composition which is proven effective in the treatment, prevention, or even reversal, of the symptoms of photoaging.

SUMMARY OF THE INVENTION

The invention relates to cosmetic or pharmaceutical compositions for topical application to the skin, the composition comprising a least one of each of the antioxidants selected from the group consisting of (a) tocopherol and derivatives thereof, (b) ascorbic acid and derivatives thereof,(c) a butylated phenol, (d)N-acetyl cysteine, (e)a rosemary extract, and (f)ubiquinone or a derivative thereof. The composition is useful in the treatment and prevention of photoaging, i.e., that damage to the skin which occurs as a result of repeated exposure to the sun.

DETAILED DESCRIPTION OF THE INVENTION

Figure 1:
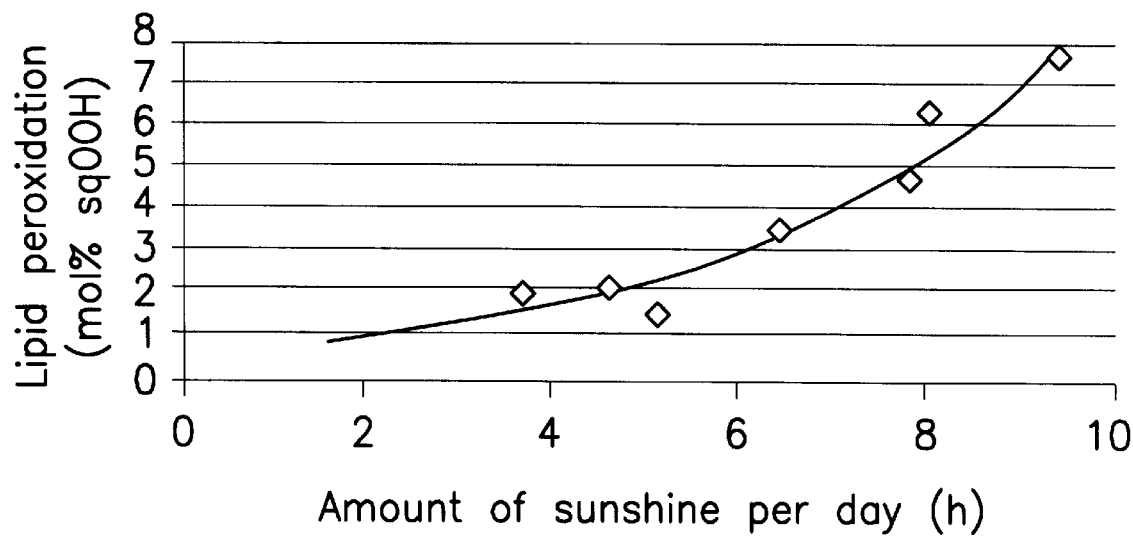
FIG. 1 illustrates the correlation between the daily amount of sunshine and the level of lipid peroxidation on the skin.

As noted above, it has definitely been recognized that various oxygen free radicals and reactive species are implicated in the damage resulting from prolonged exposure to UV radiation and other environmental insults. Various types of antioxidants have been tested experimentally to determine if they may have an ameliorating effect on UV-induced damage(Packer, L. in *Free Radical Damage and its Control*, 9: 239–255, 1994, Rice-Evans & Burton, eds., Elsevier Science B. V.; Miyachi et al. *Clin. Exp. Dermatol.* 8: 305–310, 1983; Khettab et al., *Biochimie* 70: 1709–1713, 1988; Law and Lewis, Br. *J. Pharmacol.* 59: 591–597, 1977;

Bissett et al., *Photodermatol. Photoimmunol. Photomed.* 7: 56–62, 1990). However, to date, such studies have focused on the effect of antioxidants on damage caused by acute UV exposure, and primarily on animal models. There is no previous evidence to suggest that antioxidants can have any protective effect in vivo against long-term, regular exposure to the sun.

The combination of antioxidants of the present compositions have now been unexpectedly shown to be capable of preventing the development or worsening of skin damage resulting from actual chronic sun exposure. On the molecular level, the combination, when topically applied, has been shown to provide a protective effect against lipid peroxidation on the skin surface. High lipid peroxide levels are recognized as an indicator of an acute event of oxidative stress. Clinically, the combination also has been shown to be highly effective in protecting against the development of lines and wrinkles, preventing the worsening of existing wrinkles, and to a lesser extent, even promoting some regression in existing lines and wrinkles. The combination also provides a protective effect against loss of elasticity and skin thickness which characterizes photoaging. The protective effects are particularly noticeable on chronically sun-exposed skin.

The components of the combination are known antioxidants that are either commercially available or readily prepared. All components are used in antioxidant-effective amounts, these amounts varying depending upon the identity of the compound and its potency. A first component of the combination is Vitamin E or a homologue, analog or derivative thereof. The principle active component of Vitamin E is tocopherol, particularly β-tocopherol; however, any Vitamin E or tocopherol derivative may be employed. Examples of useful derivatives are esters, for example, tocopherol acetate, tocopherol linoleate, tocopherol nicotinate, tocopherol sorbate, or tocopherol succinate; polyethylene glycol ethers of tocopherol, such as tocophereth-5, tocophereth-10, tocophereth-12, tocophereth-18 or tocophereth-50 and 6-hydroxychroman homologues, (such as are described in U.S. Pat. Nos. 4,003,919; 4,018,799; 4,026,907 and 3,903, 317)particularly 6-hydroxy-2,5,7,8-tetramethylchroman-2-chroman-2-carboxylic acid, commercially available as Trolox®-C(Cort et al., JAOCS 52: 174, 1975) and Troloxyl-amino acids(Taylor et al., JAOCS: 622, 1981).

The tocopherol derivative may also be a tocopherol-cysteamine having the formula:

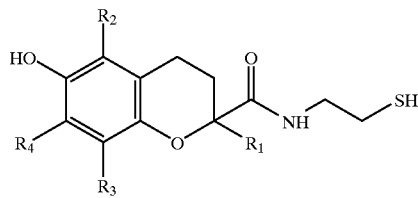

or cosmetically or pharmaceutically acceptable salts thereof, wherein $R_1$, $R_2$, $R_3$, and $R_4$ may be the same or different, and are independently selected from the group consisting of hydrogen, $C_1$–$C_{18}$ alkyl, substituted $C_1$–$C_{18}$ alkylf $C_1$–$C_{18}$ alkoxy, substituted $C_1$–$C_{18}$ alkoxy, $C_1$–$C_{18}$ alkenyl, substituted $C_1$–$C_{18}$ alkenyl, $C_1$–$C_{18}$ alkynyl, and substituted $C_1$–$C_{18}$ alkynyl. The alkyl, alkenyl, alkoxy and alkynyl groups may be straight- or branched chain, and substituted with halogen, OH, SH, $NH_2$, $NO_2$, and the like. A preferred compound is one in which $R_1$–$R_4$ are each $C_1$–$C_4$, and more preferably each is methyl. Other preferred compounds are those in which $R_1$ is methyl, and $R_3$, $R_3$, and $R_4$ are the same or different, and may be H, OH or $C_1$–$C_4$ alkyl, $C_1$–$C_4$ alkoxy, Cl, Br, F, $NO_2$, $NH_2$, or $N(R_5)_2$, wherein $R_5$ is $C_1$–$C_4$ alkyl. The tocopherol-cysteamine compounds can be made using readily available starting materials according to the following scheme:

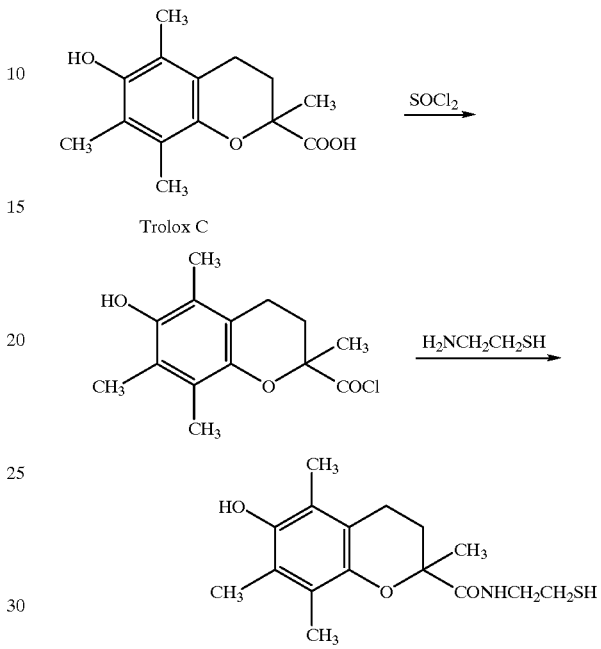

The amount of Vitamin E-related component used in the composition will vary depending upon the potency of the chosen component, but will generally be in the range of from about 0.01–20% by weight of the total composition. In one preferred embodiment, there is more than one Vitamin E component in the mixture; particularly preferred is a mixture containing both a-tocopherol and tocopherol cysteamine.

A second component is Vitamin C(ascorbic acid) or a homologue, analog or derivative thereof. The derivatives of Vitamin C which may be used are, for example, ascorbyl esters of fatty acids, such as ascorbyl palmitate, ascorbyl dipalmitate, ascorbyl dimethylsilanol palmitate, and ascorbyl stearate; metal or metal phosphate salts, such as magnesium, sodium, or potassium ascorbyl phosphate, or magnesium, sodium or potassium ascorbate. This component is typically present in an amount of from about 0.01–20% by weight, more preferably from 1–10%.

A third component is a butylated phenol, or a salt thereof. Examples include t-butyl hydroquinone, di-t-butyl hydroquinone, and BHT. Particularly preferred for use in the composition of the invention is BHT. This component is preferably used in an amount of from about 0.01–1%, preferably 0.01–0.5%, by weight of the total composition.

A fourth component is a ubiquinone(ubidecarenone) or derivative thereof. Ubiquinone is a naturally occurring hydrogen carrier in the respiratory chain(coenzyme Q); structurally, it is a 2,3-dimethoxy-5-methyl-1,4-benzoquinone with a multiprenyl side chain, the number of isoprene units varying depending upon the organism. The composition may contain any ubiquinone, or combinations thereof, or may also be represented as the reduced form, ubiquinol. Other ubiquinone derivatives are described, for example, in WO 8803015. The ubiquinone component is preferably employed in an amount of from about 0.01–1%, preferably 0.01–0.5% by weight of the total composition.

A fifth component is N-acetyl-L-cysteine. This is compound having the formula:

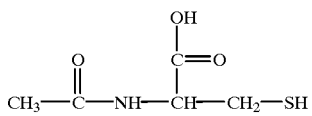

N-acetyl cysteine is used in the composition in an amount of from about 0.01–20% by weight of the total composition.

A final component of the combination is a rosemary extract, by which is meant the whole extract, or an active fraction thereof. Preferably the extract is an oil-soluble extract. Such rosemary extracts are commercially available from a variety of manufacturers. The preferred antioxidant fraction of the extract are primarily in the dehydroabeitic acid class of diterpenes. Among the specifically identified active ingredients of the extract are carnosol, carnosic acid and rosmanol. However, there are other unidentified components of the extract which also possess antioxidant activity, and these may also be used in the composition. The preferred extract is one which contains from about 1–5% carnosic acid, from about 2–7% carnosol, and from about 0.1–1% rosmanol; such an extract is commercially available under the tradename Stabex™, from SKW Chemicals. An extract of this type can be used in an amount of from about 0.0001 to about 1%, preferably about 0.005–0.5%, more preferably from about 0.01–0.1%, by weight of the total composition. However, it will be understood that the composition may also simply use one or more of the individual components of the useful extracts.

For topical application, the antioxidant mixture can be combined with a cosmetically and/or pharmaceutically acceptable carriers. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1,3-diol, isopropyl myristate, isopropyl palmitate, or mineral oil. Methodology and components for formulation of cosmetic and pharmaceutical compositions are well known, and can be found, for example, in Remington's Pharmaceutical Sciences, Eighteenth Edition, A. R. Gennaro, Ed., Mack Publishing Co. Easton Pa. 1990. The carrier may be in any form appropriate to the mode of delivery, for example, solutions, colloidal dispersions, emulsions(oil-in-water or water-in-oil), suspensions, creams, lotions, gels, foams, mousses, sprays and the like.

The formulation, in addition to the carrier and the antioxidant mixture, also can comprise other components which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like. As will be apparent, the composition can be a therapeutic product the antioxidants being the sole actives, or in combination with other actives. However, the composition can also be a makeup product, for example, a lipstick, foundation, concealer, bronzer, blush, eyeshadow and the like.

In one preferred embodiment, the composition also contains a sunscreen. The combination may be with any sunscreen. Examples of sunscreens useful in the compositions include, but are not limited to, inorganic sunscreens such as titanium and zinc oxides, or organic sunscreens such as para-amino benzoic acid(PABA)and its esters, benzophenones, phenyl or homomenthyl salicylates, and cinnamates. In such a composition, the sunscreen of choice is employed in an amount consistent with the established use of that sunscreen.

The compositions of the invention can be applied on an as-needed basis, for example, applied to the skin before anticipated prolonged sun exposure, or during or after such exposure. However, as the best results are achieved after regular application over a period of time, a preferred method of obtaining the benefits of the composition is via chronic topical application of a safe and effective amount of a composition containing the mixture, to prevent development of skin damage which may result from even routine exposure to UV light or other environmental insults which may result in the generation of reactive oxygen species, or to prevent worsening of or to reverse existing damage. It is suggested as an example that topical application of the composition, in an amount of from about 0.1 $\mu g/cm^2$ to 2 $mg/cm^2$ of exposed skin, be performed from about once per week to about 4 or 5 times daily, preferably from about 3 times a week to about 3 times daily, most preferably about once or twice per day. By "chronic" application, it is meant herein that the period of top4cal application may be over the lifetime of the user, preferably for a period of at least about one month, more preferably from about three months to about twenty years, more preferably from about six months to about ten years, more preferably still from about one year to about five years, thereby resulting in the treatment or prevention of the external signs of photoaging. It will be recognized by those skilled in the art that the treatment regimen employed can be varied depending upon the user's level of exposure to noxious stimuli; a chronically sun-exposed individual may benefit from more frequent applications than will be necessary for an individual who avoids the sun.

EXAMPLES

I. Clinical Studies

A. Experimental Design. A clinical study conducted over a period of 18 months involved a total of 160 female volunteers, 35 to 45 years of age. The volunteers are selected from three locations with distinct climatological conditions: one is a mountainous area, subject to a considerable amount of pollution; one has a very mild climate; and one is an area frequently subject to large variation in temperature. In the evaluation, the skin lipid peroxide level is chosen as a biochemical marker for the early events of oxidative damage. In addition, to provide a link with the clinical signs of premature aging, a visual grading of wrinkling and sagging is performed by an expert dermatologist, and skin thickness and elasticity are measured by echography and cutometry, respectively, on the subgroup from the area of mild climate.

B. Methods. Topical treatment with an emulsion containing 2% tocopheryl acetate, 0.1% rosemary extract, 0.1%

BHT, 0.5% N-acetyl cysteine, 1% magnesium ascorbye phosphate, 0.1% ubiquinone, and 0.1% tocopherol cysteamine, was performed twice a day on the left forearm and face. The right arm served as an untreated control.

Skin lipid peroxide value, skin thickness, skin elasticity and dryness were measured on chronically sun exposed (face, dorsal forearm) and unexposed (ventral forearm) sites. Wrinkle formation was monitored on the face.

To rule out effects which are not due to the treatment, each person acted as her own control. For measurements on the forearm, the right (untreated) arm served as a control for the left (treated) one. Then the effect of the treatment can be expressed as:

ventral: $\Delta V$ (difference between Left and Right Ventral) at timepoint $Mx=(LV-RV)_{Mx}$ dorsal: $\Delta D$ (difference between Left and Right Dorsal) at timepoint $Mx=(LD-RD)_{Mx}$ It is more relevant to present these values as a percentage difference ($\%\Delta V$ on ventral side and $\%\Delta D$ on dorsal side) between the arms at a given timepoint Mx, with positive figures meaning that the left arm has a higher value (more lipid peroxides, thicker skin, more elastic skin) than the right arm:

ventral: $\%\Delta V$ at $Mx=(LV-RV)_{Mx}/LV_{Mx} \times 100\%$ dorsal: $\%\Delta D$ at $Mx=(LD-RD)_{Mx}/LD_{Mx} \times 100\%$ The overall effect of the treatment at each timepoint Mx is then corrected for the baseline value M0.

On the forehead, there is no internal untreated control, but the evolution in the treated group can be compared to the control group.

The skin lipid peroxide value is quantified by HPLC as the molar percentage of squalene hydroperoxide over residual squalene in an ethanolic extract of skin surface lipids.

Severity of wrinkles is evaluated by a visual scoring system guided by photographs representing different photograding classes going from 1 (mild) to 5 (severe). Additionally, image analysis of silicone eye zone replicas provided an overall assessment of skin surface topography and texture.

Cutaneous thickness (epidermis+dermis) is measured by an ultrasound technique (echography 20 MHz) and expressed in mm.

Cutaneous elasticity is expressed as the ability of the skin to vertically extend when suction is applied by a cutometer. The immediate deformation of the skin is quantified by optical means.

Moisturization of the skin is reflected in the skin's capacitance (corneometer), which measures the moisture content of the superficial layers of the epidermis. Additionally, the smoothness of the skin's surface is clinically evaluated on the face (Kligman score).

C. Results

1. Skin Lipid Peroxidation 1.a. Influence of Casual UV Exposure

A professional meteorological institute provided information on the weather conditions during the test period in each of the centers. Average hours of sunshine have been compared to the squalene peroxide level on the right (untreated) dorsal (potentially sunexposed) arm.

As shown in FIG. 1, it was found that the skin lipid peroxidation level was very well correlated with the average amount of sunshine per day, provided that the ambient temperature is high enough to allow incident exposure df the arms (average temperature above 10° C.).

As a result of this, the skin lipid peroxide level is a highly variable parameter. It has for example been shown to range from values as low as 0.2 mol % up to 44 mol % squalene peroxide in the same panelist over a period of 6 months.

1.b. Influence of Topical Antioxidants

Figure 2:
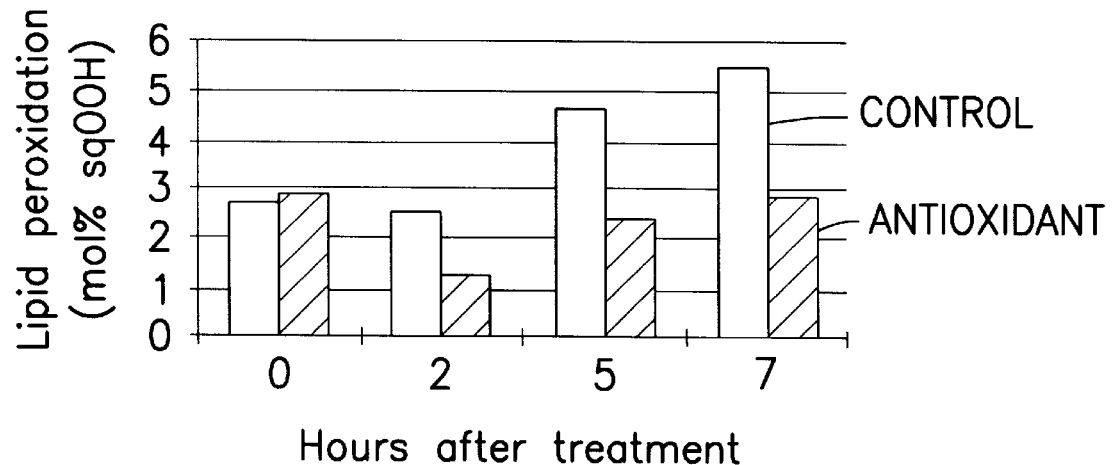
FIG. 2 demonstrates the immediate effect of antioxidant treatment on the lipid peroxidation level on the skin.

IMMEDIATE EFFECT:

Topical antioxidant treatment has an immediate impact on the skin lipid peroxide level. The lipid peroxidation level is highly significantly reduced up to at least seven hours after the application, as shown in FIG. 2.

Figure 3:
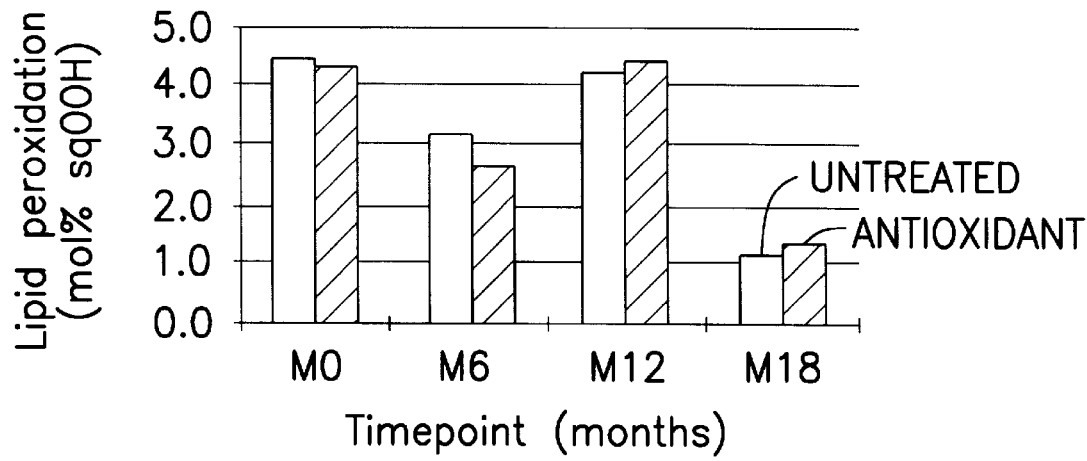
FIG. 3 demonstrates the long term effect of antioxidant treatment on lipid peroxidation level on the skin.

LONG TERM EFFECT:

However, the baseline peroxidation level is not affected by the antioxidant treatment once the antioxidants have penetrated into the skin or have been consumed. All panelists were requested to interrupt the topical treatment for at least 24 hours when they were called in for examination. At that moment, no significant difference(FIG. 3) in lipid peroxide level can be seen between a previously antioxidant treated and an untreated arm.

2. Clinical Evaluation of Lines and Wrinkles 2.a. Visual Grading

A discontinuous scaling system guided by a set of photographs is used for the clinical evaluation of visual signs of photodamage on the face. The scores range from 1 (mild) to 5 (severe).

Figure 4:
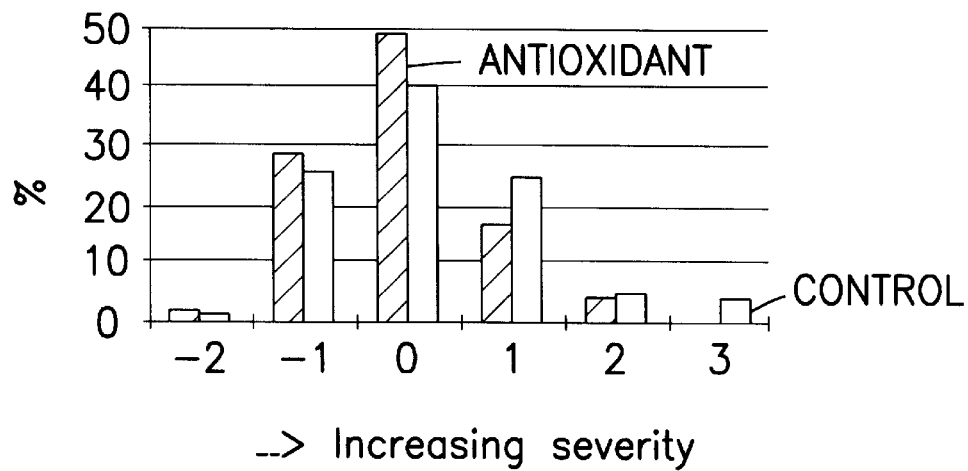
FIG. 4 compares the evolution of facial lines and wrinkles, over a period of 18 months, between individuals treated with a composition of the invention, and untreated individuals.

The evolution of all individual scores is reflected in the graphs(FIG. 4) showing the percentage of panelists for whom the grading score shifted with a specified number of classes. A negative shift corresponds to an improvement of existing lines and wrinkles.

The global evolution of each group can be expressed as a weighted score, giving more weight to larger individual shifts than to smaller ones. A negative weighted score will then reflect a global evolution towards a lower photograding class, meaning that more volunteers in this group show a regression of existing wrinkles than there are panelists with an increase in wrinkles, as is the case for the antioxidant treated group.

Figure 5:
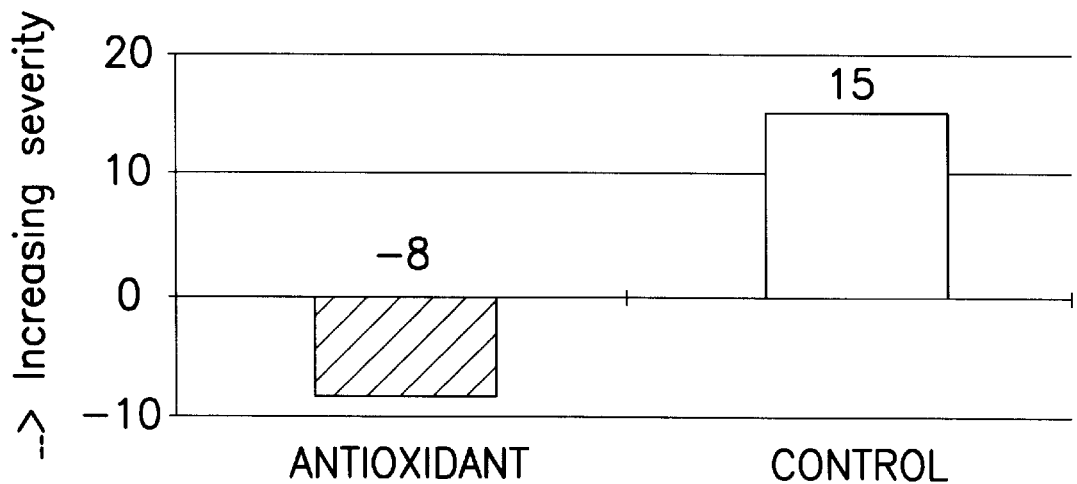
FIG. 5 compares the global evolution of facial lines and wrinkles as shown in FIG. 4, as a weighted score.

As seen in FIG. 5, the group applying the topical antioxidants shows an important tendency for stabilization of existing lines and wrinkles and even some regression, compared to the control group where a global increase of the wrinkles with 15% was seen over a period of 18 months.

2.b. Replica Analysis

Figure 6:
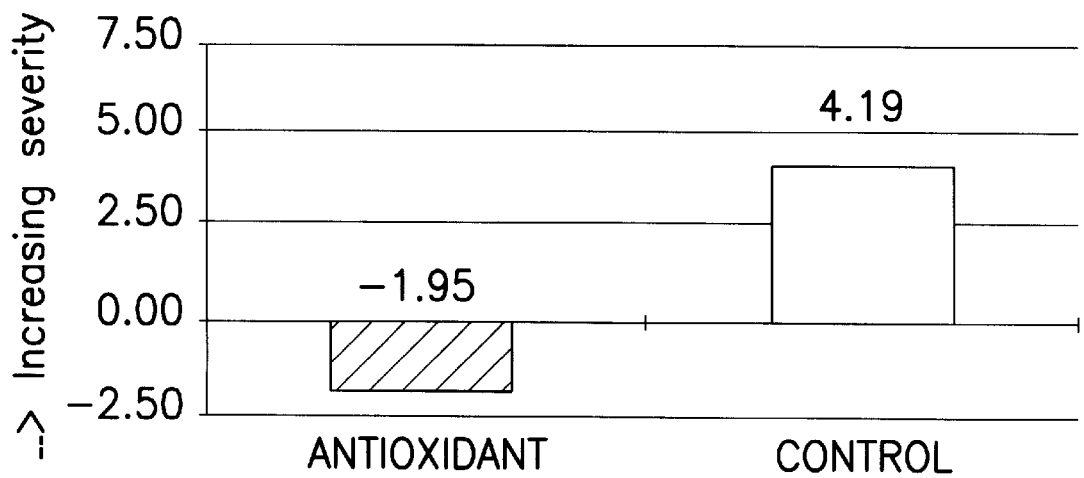
FIG. 6 shows a graphic analysis of increase in severity of crows feet eye replicas in treated and control groups.
Figure 7:
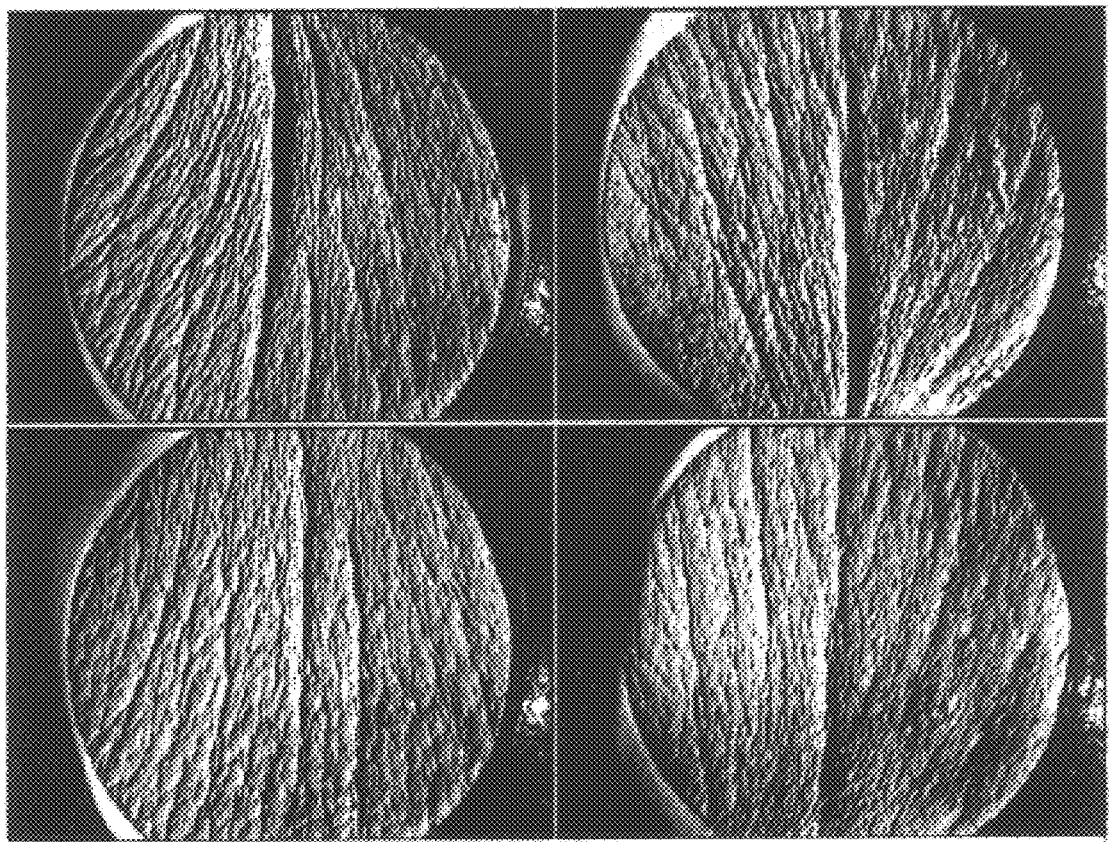
FIG. 7 shows a photograph of image analysis of silicone replicas of the crows feet area for one panelist in the treatment group. Top: baseline; Bottom: after 18 months of treatment.
Figure 8:
FIG. 8 shows the actual image analysis of silicone replicas of the crows feet area for one panelist in the control group. Top: baseline; Bottom: after 18 months.

Image analysis was conducted on silicone eye replicas. The resulting data provide an overall assessment of skin surface topography and texture. The average change over a period of 18 months in the antioxidant treated and the control group indicates again a protective effect from the topical antioxidants towards wrinkle progression and even some regression of existing wrinkles(FIGS. 6, 7 and 8).

These results show that it is possible to improve the skin's structure by providing strong daily protection with antioxidants, without the help of ingredients which increase collagen production in the skin.

3. Skin Thickness

For measurements on the forearms, the right (untreated) arm serves as internal control for the left (treated) arm. The difference in thickness (dermis plus epidermis) between the arms has been followed over the total period of 18 months and was compared for the two groups.

Figure 9:
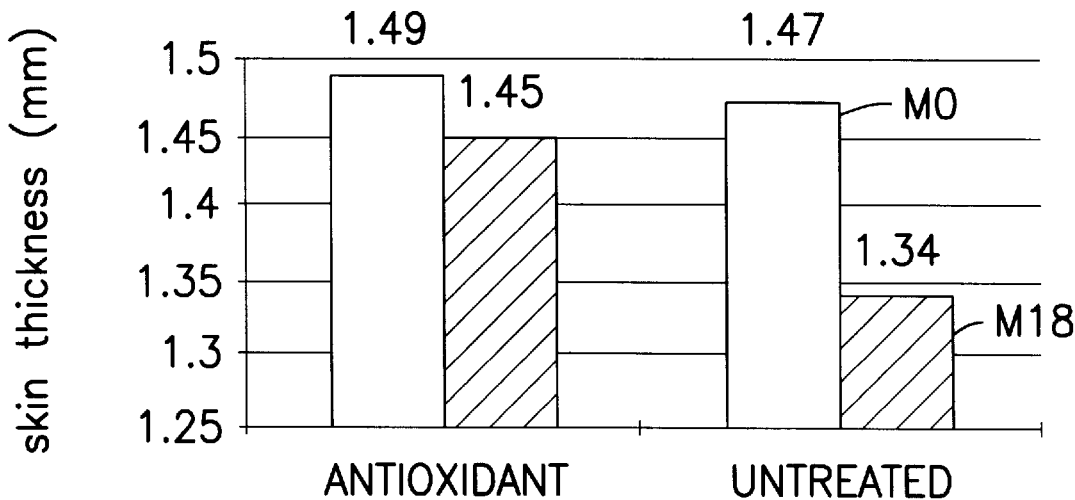
FIG. 9 illustrates the evolution of skin thickness over a period of 18 months in treated and untreated arms among treated panelists.

At baseline the thickness of the skin is similar for both arms in the antioxidant treated group. After 18 months, however, a highly significant difference in thickness is observed between the two arms, meaning that the antioxidants have provided a highly significant protection against loss of skin tissue(FIG. 9).

Figure 10:
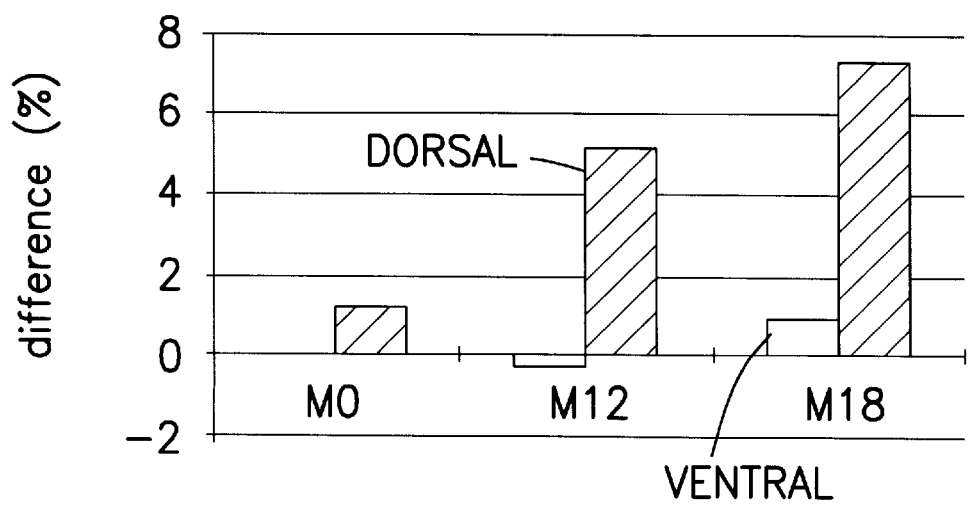
FIG. 10 illustrates the percent difference in skin thickness between treated and untreated arms among treated panelists over a period of 18 months.

This protective effect builds up over time(FIG. 10), and is most pronounced on the chronically sun-exposed side of the arm (dorsal).

Figure 11:
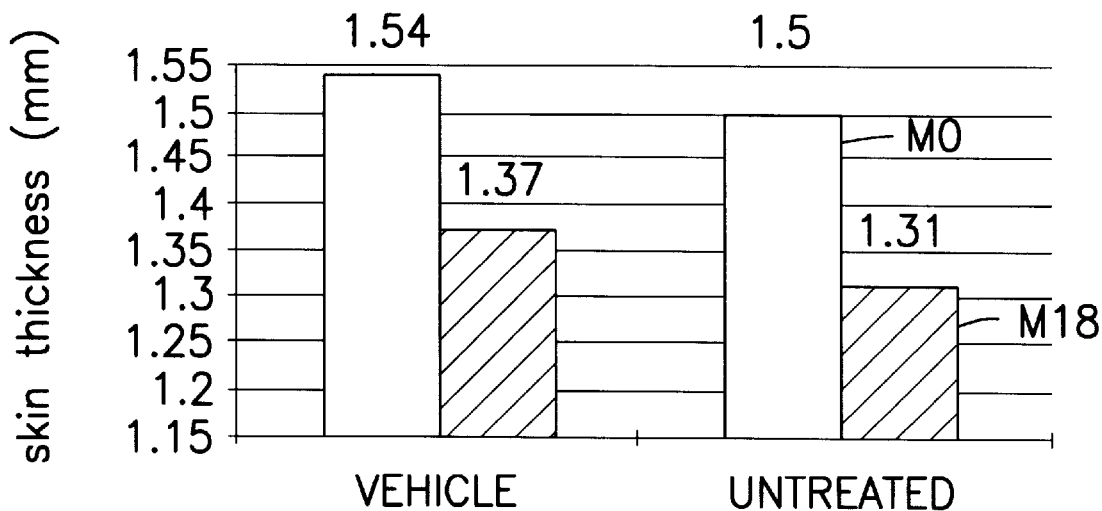
FIG. 11 illustrates the evolution of skin thickness over a period of 18 months on the arms of the control group, showing the effect of the vehicle.

The control group experiences some benefit from the vehicle treatment, although the protection against thinning of the skin is much less pronounced(FIG. 11).

Figure 12:
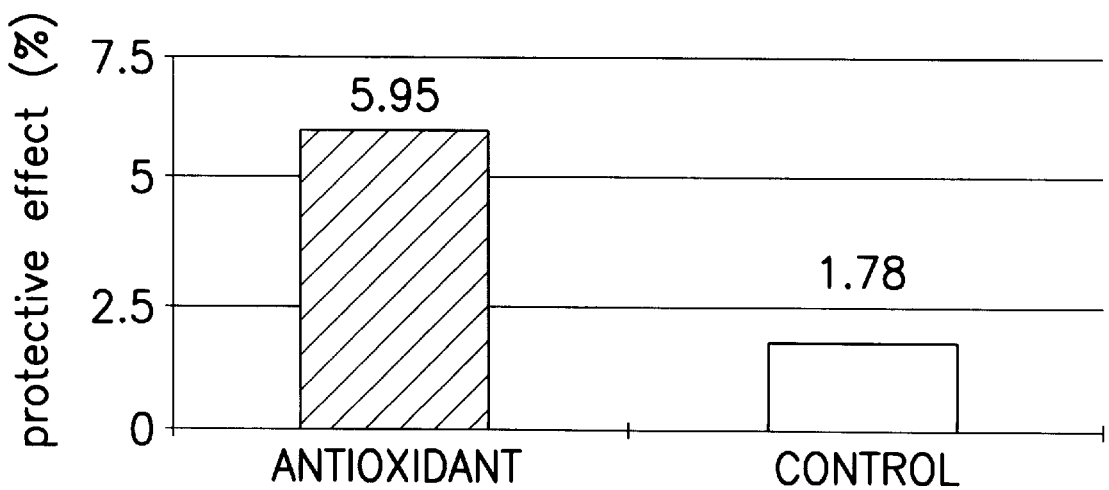
FIG. 12 compares the protective effect of the treatment with the protective effect of the control vehicle against loss of skin thickness.

Comparison of the protective effect against thinning of the skin, provided by the vehicle and the antioxidant containing formulation shows that the effect from the antioxidant containing product is about three times more important(FIG. 12).

Such a result indicates that the protection, provided by regular application of the antioxidants, prevents the UV induced destruction of the collagen in the dermis, hence reducing one of the landmarks of the aging process: the thinning of the skin.

Measurements on the forehead can not be compared to an untreated control since the face was treated over the total surface. Therefore the skin thickness was measured at baseline and at the end of the study, and the evolution in the antioxidant treated group is compared to evolution in the control group.

Figure 13:
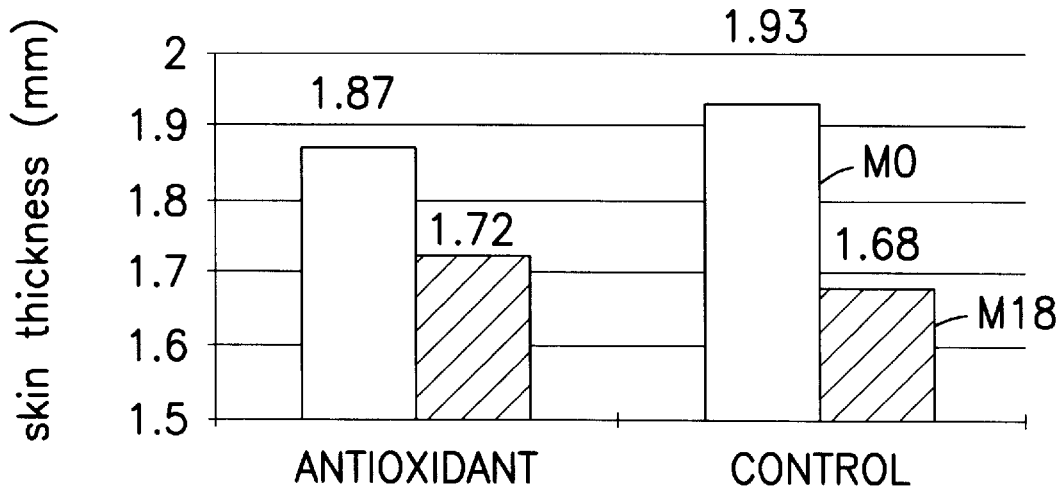
FIG. 13 compares the evolution of skin thickness on the forehead between treated and control groups over a period of 18 months.

Again the protective effect of the antioxidants is suggested from these results, since the thinning of the skin at the level of the forehead is slower in the antioxidant treated group than in the control group(FIG. 13).

4. Skin Elasticity

Figure 14:
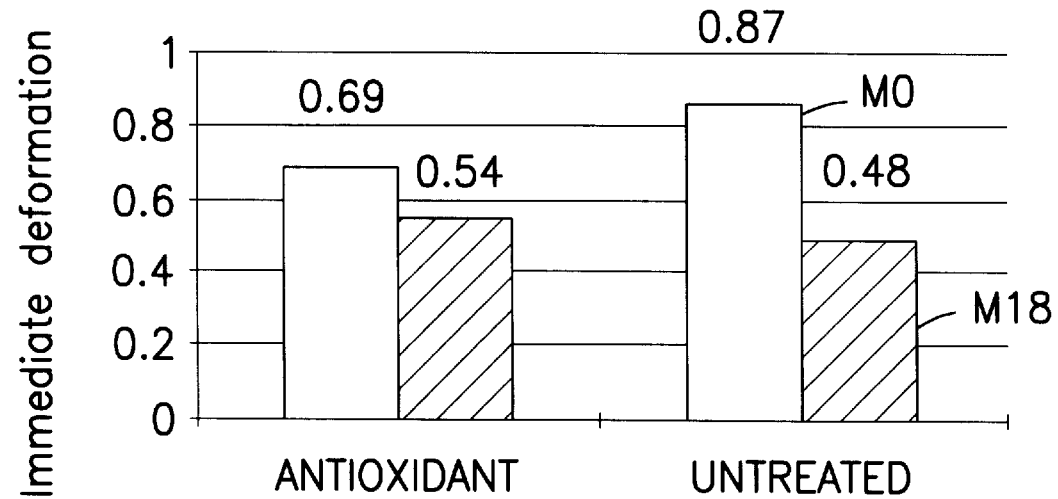
FIG. 14 compares the evolution of skin elasticity over a period of 18 months in treated and untreated arms of the treatment group.
Figure 15:
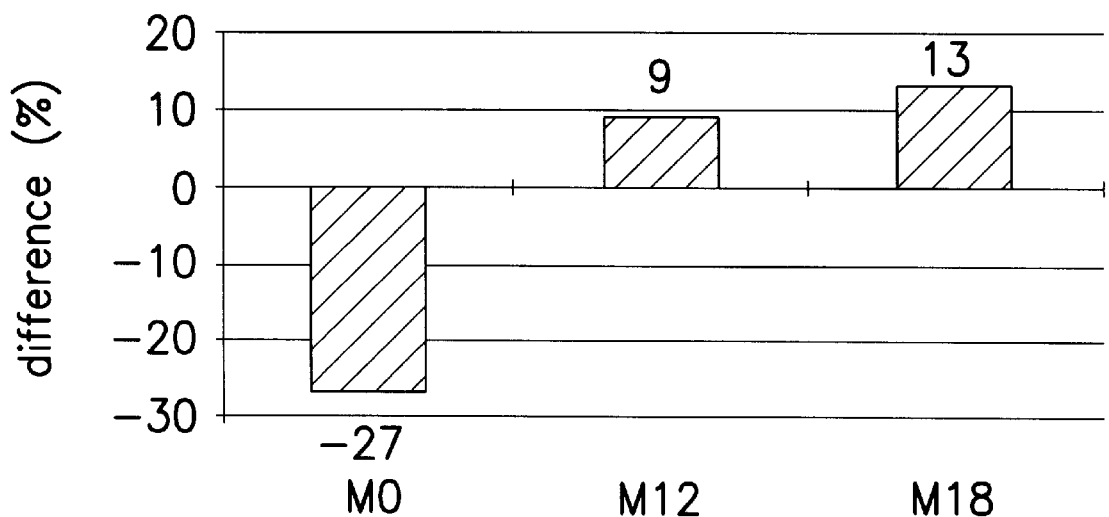
FIG. 15 compares the percent difference in skin elasticity between antioxidant treated and untreated arms in the treatment group.

The right (untreated) arm serves as internal control for measurements on the left (treated) arm. The values found on the two arms have been followed for 18 months and the evolution was compared for the treated and control groups. As was the case for the skin thickness, the skin elasticity seems to be affected by the aging process, and goes down significantly over a period of 18 months. At baseline the skin was found to be less elastic on the left than on the right arm for the treated group. However, after 18 months the skin on the untreated right arm has lost so much of its elasticity that it has now become less elastic than the left (treated) arm (FIG. 14). The antioxidant treatment provides an important protection against this loss of elasticity. The protective effect increases with the length of the treatment, and is most important on the chronically sun-exposed side of the arm (dorsal)(FIG. 15).

Figure 16:
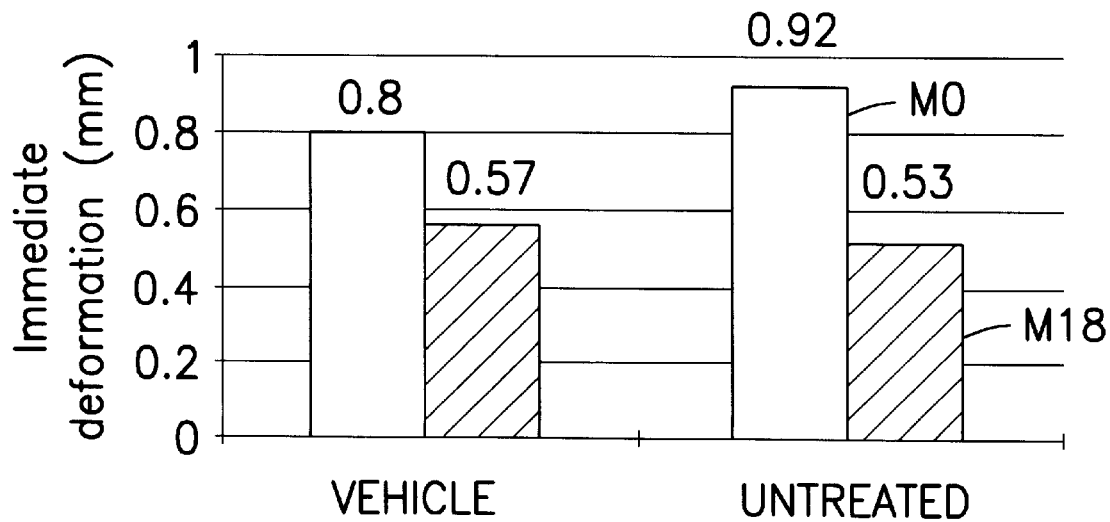
FIG. 16 illustrates the evolution of skin elasticity over a period of 18 months in the control group, showing the effect of the vehicle.
Figure 17:
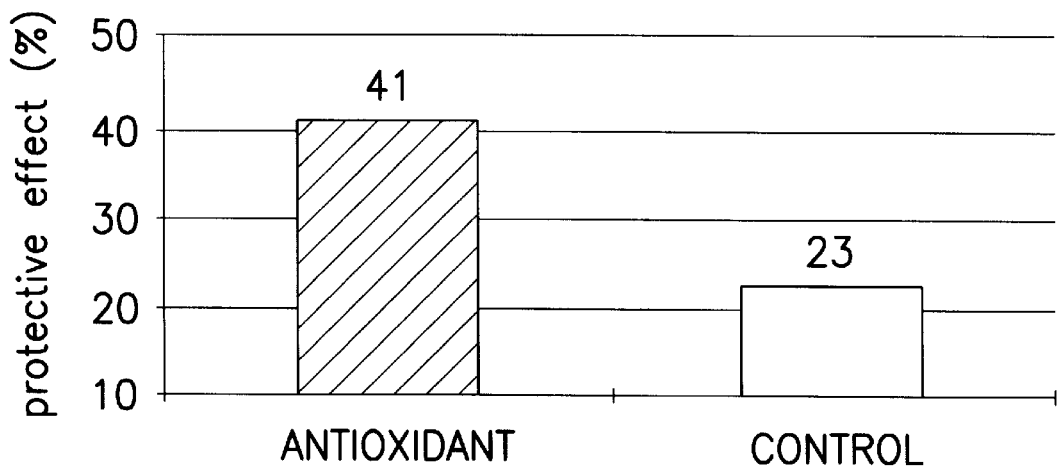
FIG. 17 illustrates the protective effect against loss of skin elasticity of the antioxidant treatment compared with that of the control.

The control group shows that regular application of a moisturizing formulation can already provide protection against loss of elasticity, although the effect is less pronounced than in the antioxidant treated group(FIG. 16). Comparison of the effect experienced in both groups shows that the protection against loss of elasticity of the antioxidant treatment is about twice as important as the effect measured for the vehicle(FIG. 17).

As a normal consequence of the protective benefits obtained from the treatment with the antioxidants, we have been able to show a highly significant protection against the loss of skin elasticity for the panelists who were treated with the antioxidant containing preparation.

5. Clinical Evaluation of Skin Dryness 5.a. Visual Grading

Figure 18:
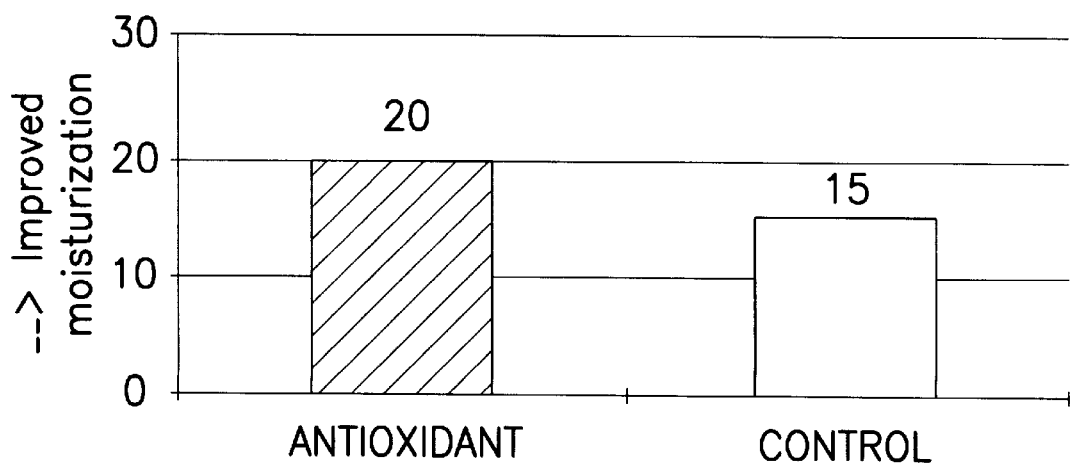
FIG. 18 shows the global evolution of moisturization in treated and control groups, as a weighted score.

The Kligman scoring system is used for the evaluation of visual smoothness of the skin's surface on the face, with a dryness scale going from 0 (smooth) to 3 (severe dryness). The global evolution of the treated and control groups has been calculated as a weighted score, giving more weight to larger individual shifts than to smaller ones. A positive weighted score in this case reflects an improvement of the skin's aspect of smoothness. As shown in FIG. 18, both groups have experienced a similar moisturizing effect from the topical treatment and show a reduction in skin dryness after 18 months.

5.b. Epidermal Moisturization

Figure 19:
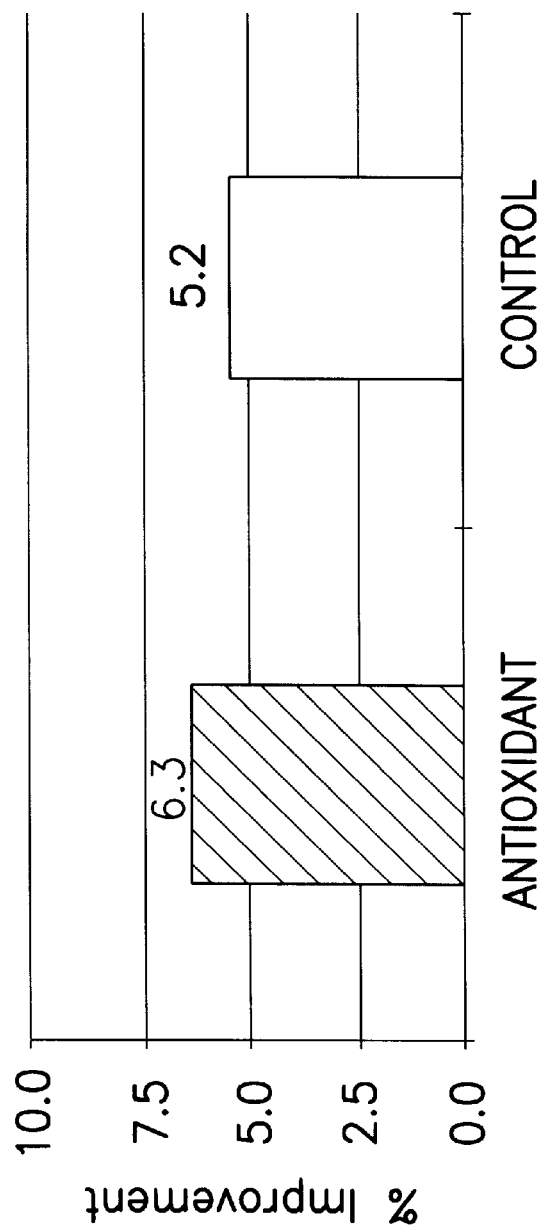
FIG. 19 compares the measurements of epidermal moisture content in treated and control groups.

This result is confirmed by measurements of the epidermal moisture content on the forearms using a corneometer, where the right arms serves as untreated control for the left one(FIG. 19).

CONCLUSIONS

The results show that the topical application of antioxidants immediately reduces the lipid peroxidation level on the skin. The baseline level of lipid peroxidation is not affected by this treatment once the antioxidants have penetrated into the skin or have been consumed.

Long term beneficial effects of the treatment are clearly evident after one year and become more pronounced after 18 months of treatment. The regular application of antioxidants prevents most of the UV induced destruction of collagen in the dermis, resulting in a protection against loss of elasticity and thinning of the skin. The process of line and wrinkle formation is slowed down, which even allows the skin cells to repair some of the damages generated,prior to the application of the treatment.

Therefore, a reasonable conclusion from the results obtained after 18 months of daily application of a topical preparation containing antioxidants is that such application can lead to long term protection benefits for the skin and retarding of the photoaging process.

What we claim is:

1. A cosmetic or pharmaceutical composition for topical application to the skin which comprises (a)from about 0.01 to about 20% of tocopherol and/or a tocopherol derivative; (b)from about 0.01 to about 20% of ascorbic and/or a derivative thereof; (c) from about 0.01 to about 0.5% of a butylated phenol; (d) from about 0.01 to about 20% of N-acetyl cysteine; (e) from about 0.0001 to about 1% of a rosemary extract, the extract comprising from about 1 to about 5% carnosic acid, from about 2 to about 7% carnosol, and from about 0.1 to about 1 rosmanol, and (f)ubiquinone and derivatives thereof.

2. The composition of claim 1 which comprises tocopherol and tocopherol cysteamine, and an ascorbyl phosphate.

3. A method for treating or preventing the symptoms of photoaging on the skin comprising applying to the skin a composition according to claim 1.

4. The method of claim 3 in which the composition is applied about once or twice daily.

5. The method of claim 4 in which the composition is applied over a period of from about three months to about twenty years.

6. A method for treating, preventing, or reducing lines and wrinkles on the skin which comprises applying to the skin a composition according to claim 1.

7. A method for treating or preventing loss of elasticity in the skin which comprises applying to the skin a composition according to claim 1.

8. A method for treating or preventing skin thinning which comprises applying to the skin a composition according to claim 1.

9. A method for treating or preventing skin dryness which comprises applying to the skin a composition according to claim 1.

10. The composition of claim 1 which comprises a tocopherol derivative.

11. The composition of claim 1 in which the ascorbic acid derivative is an ascorbyl phosphate.

12. The composition of claim 1 in which the butylated phenol is BHT.

13. The composition of claim 1 which contains tocopheryl acetate, tocopherol cysteamine, and an ascorbyl phosphate.

14. The composition of claim 13 which comprises magnesium ascorbyl phosphate.

15. The composition of claim 1 which comprises (a) β-tocopherol and tocopherol cysteamine, (b) an ascorbyl phosphate, (c) BHT, (d) N-acetyl cysteine, (e) a rosemary extract comprising at least one antioxidant selected from the group consisting of carnosic acid, carnosol, and rosmanol, and (f) ubiquinone.

* * * * *